United States Patent [19]
Hennings et al.

[11] Patent Number: 5,591,157
[45] Date of Patent: Jan. 7, 1997

[54] METHOD AND APPARATUS FOR TYMPANIC MEMBRANE SHRINKAGE

[76] Inventors: David R. Hennings, 190 Welcome Rd., New Castle, Calif. 95658; Arthur V. Vassiliadis, 720 Morningside; Richard L. Goode, 440 Old Oak Ct., both of Los Altos, Calif. 94022; Bruce J. Sand, 24922 Jim Bridge Rd., Hidden Hills, Calif. 91302; Stuart Harmon, 4321 Beechmont Ave., San Jose, Calif. 95136

[21] Appl. No.: 301,911

[22] Filed: Sep. 7, 1994

[51] Int. Cl.⁶ ..................................................... A61H 5/06
[52] U.S. Cl. .................................. 606/3; 606/10; 606/13; 606/15
[58] Field of Search ...................... 606/2, 3–19

[56] References Cited

U.S. PATENT DOCUMENTS

| | | |
|---|---|---|
| 4,672,969 | 6/1987 | Dew . |
| 4,676,796 | 6/1987 | Merwin et al. . |
| 4,854,320 | 8/1989 | Dew et al. . |
| 4,950,266 | 8/1990 | Sinofsky ................................. 606/7 |
| 4,976,709 | 12/1990 | Sand . |
| 5,002,051 | 3/1991 | Dew et al. . |
| 5,140,984 | 8/1992 | Dew et al. . |
| 5,280,378 | 1/1994 | Lombardo . |
| 5,281,211 | 1/1994 | Parel et al. . |
| 5,304,169 | 4/1994 | Sand . |

FOREIGN PATENT DOCUMENTS 2003326 11/1993 Russian Federation .

OTHER PUBLICATIONS

Lesinski, S. G., et al.; "Carbon dioxide lasers for otosclerosis"; *Otolaryngol. Clin. North Am.*; vol. 26, No. 3; Jun., 1993; pp. 417–441.

McKennan, K. X.; "'Tissue welding' with the argon laser in middle ear surgery"; *Laryngoscope;* vol. 100, No. 11; Nov., 1990; pp. 1143–1145.

Mishen'kin, N. V., et al.; "Effects of helium–neon laser energy on the tissues of the middle ear in the presence of biological fluids and drug solutions" (with English translation of abstract); *Vestn. Otorinolaringol (USSR)*; vol. 5; Sep.–Oct., 1990; pp. 18–21.

Fried, M. P., et al.; "Head and neck applications of the milliwatt laser"; *Lasers Surg. Med.;* vol. 7, No. 1; 1987; pp. 46–50.

*Primary Examiner*—David M. Shay
*Attorney, Agent, or Firm*—Majestic, Parsons, Siebert & Hsue

[57] ABSTRACT

The tympanic membrane can be tightened by directing energy on spots of the tympanic membrane so as to heat up the collagen matrix layer and cause it to shrink. Energy in the frequency range of 1.4 to 2.6 microns, which roughly corresponds to a collagen absorption range of from 10 to 150 $cm^{-1}$, is used.

42 Claims, 11 Drawing Sheets

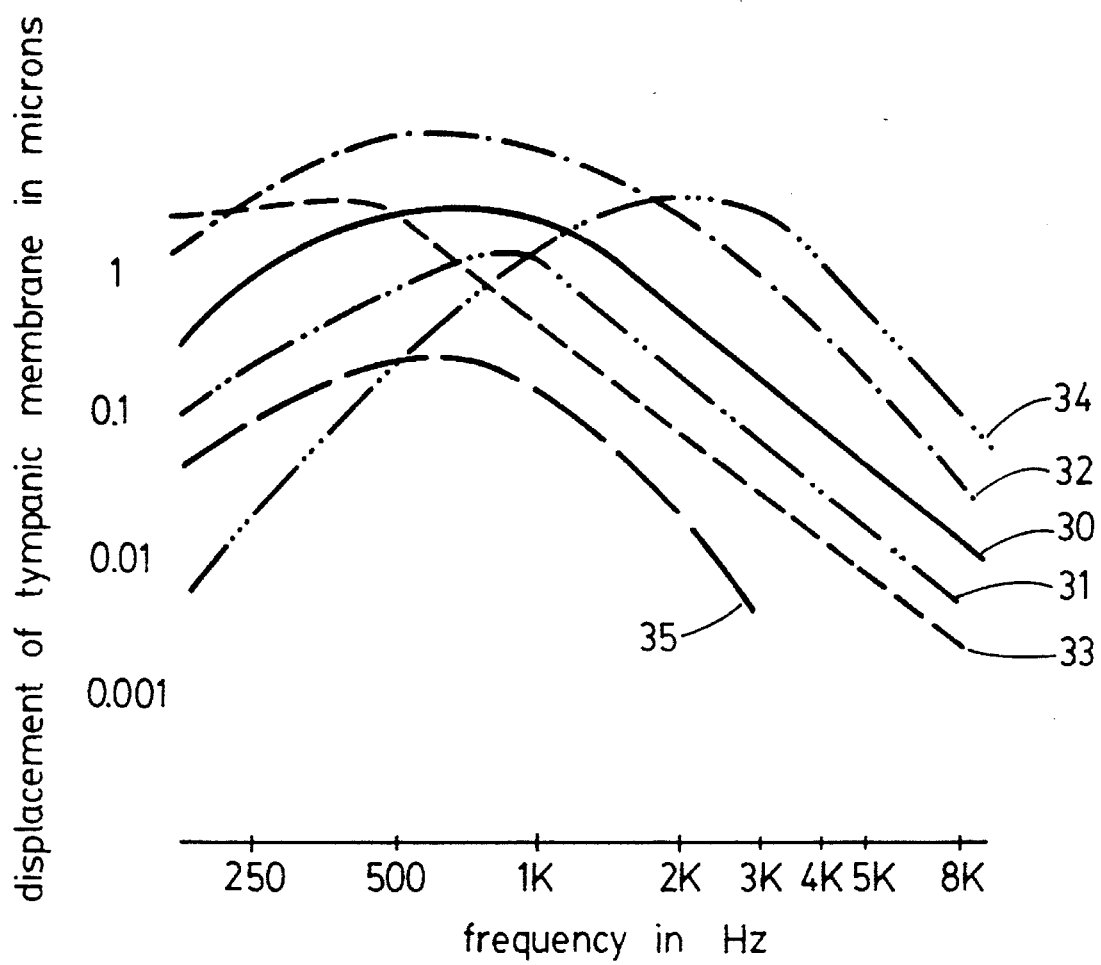
FIG._1.

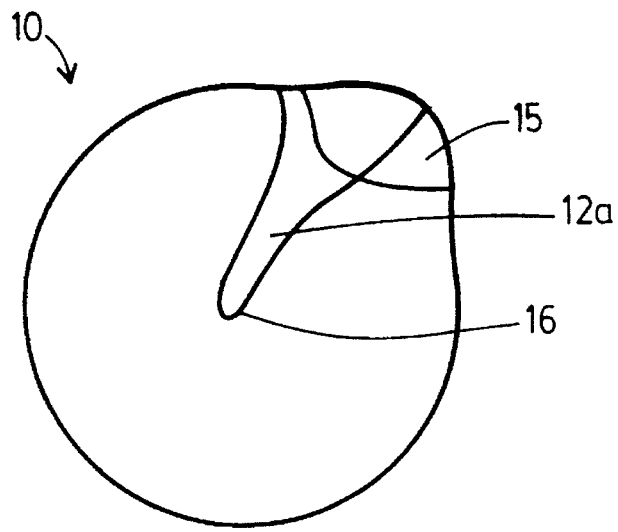
FIG._2A.
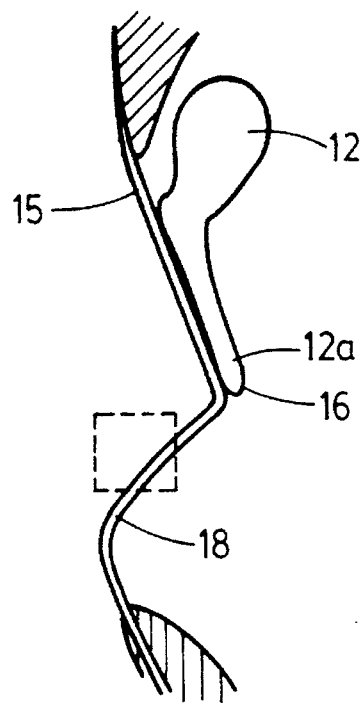
FIG._2B.
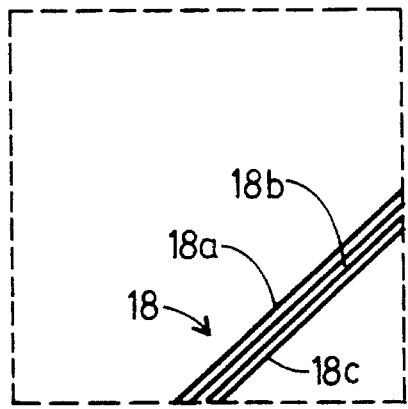
FIG._2C.

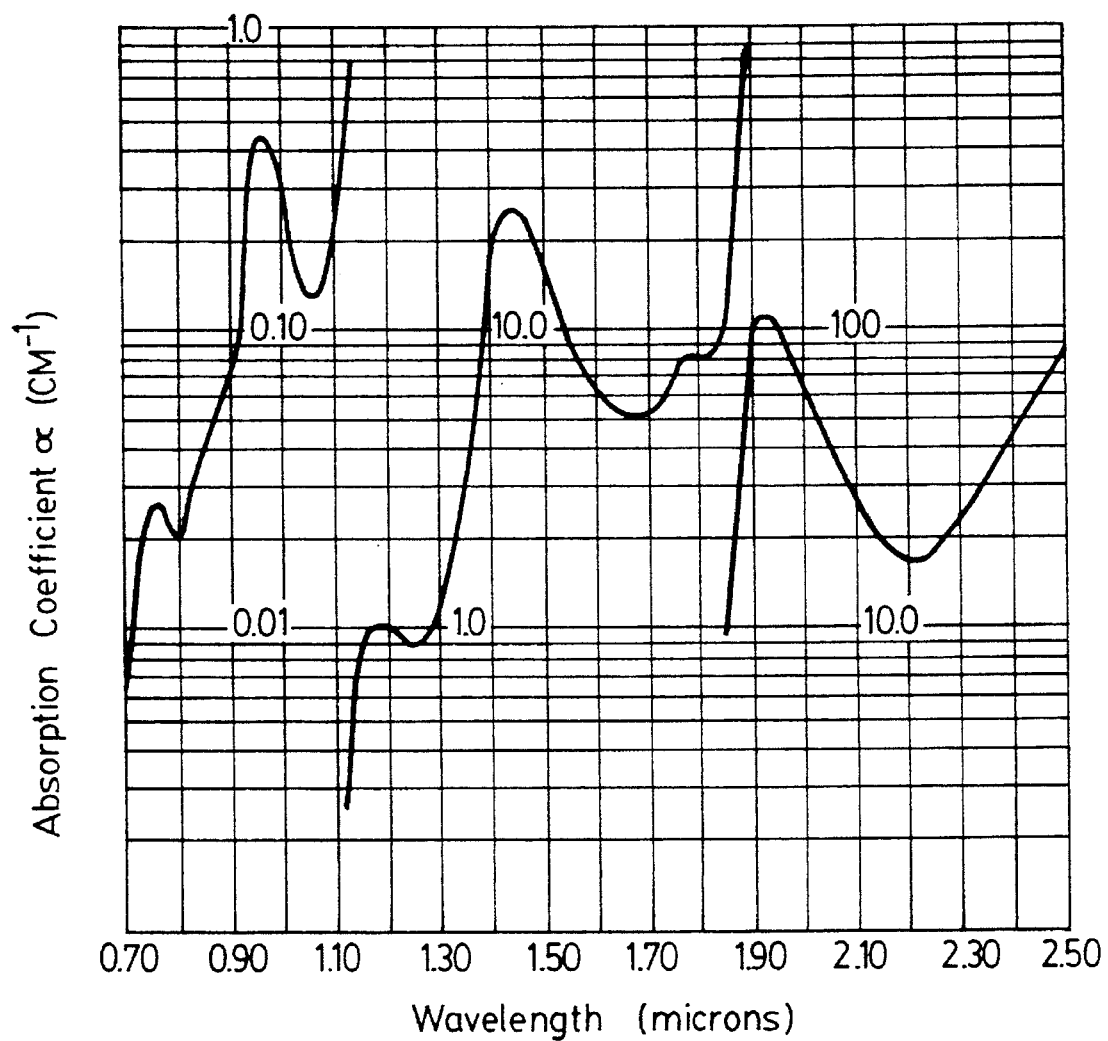
FIG._3.

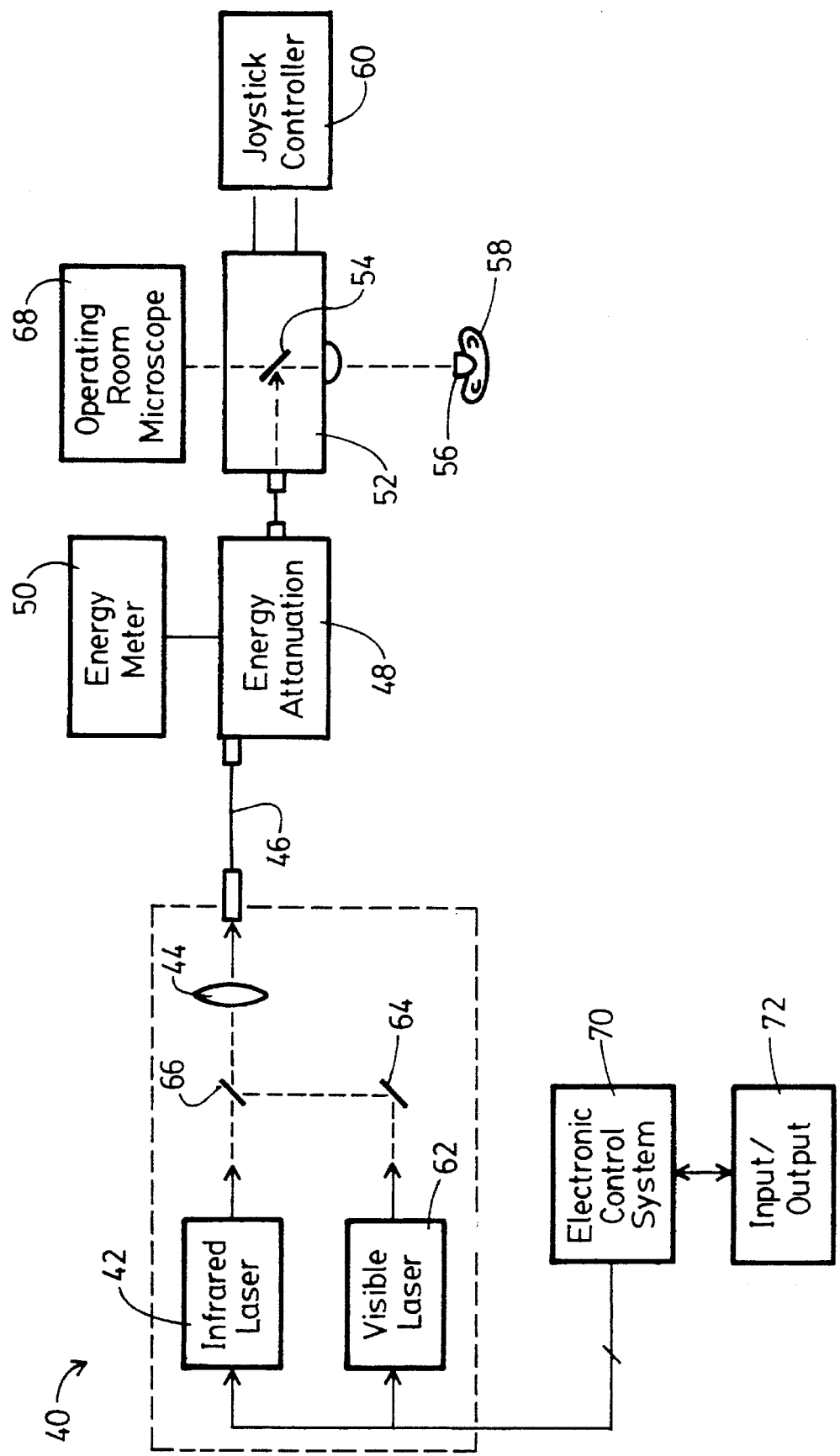
FIG._4.

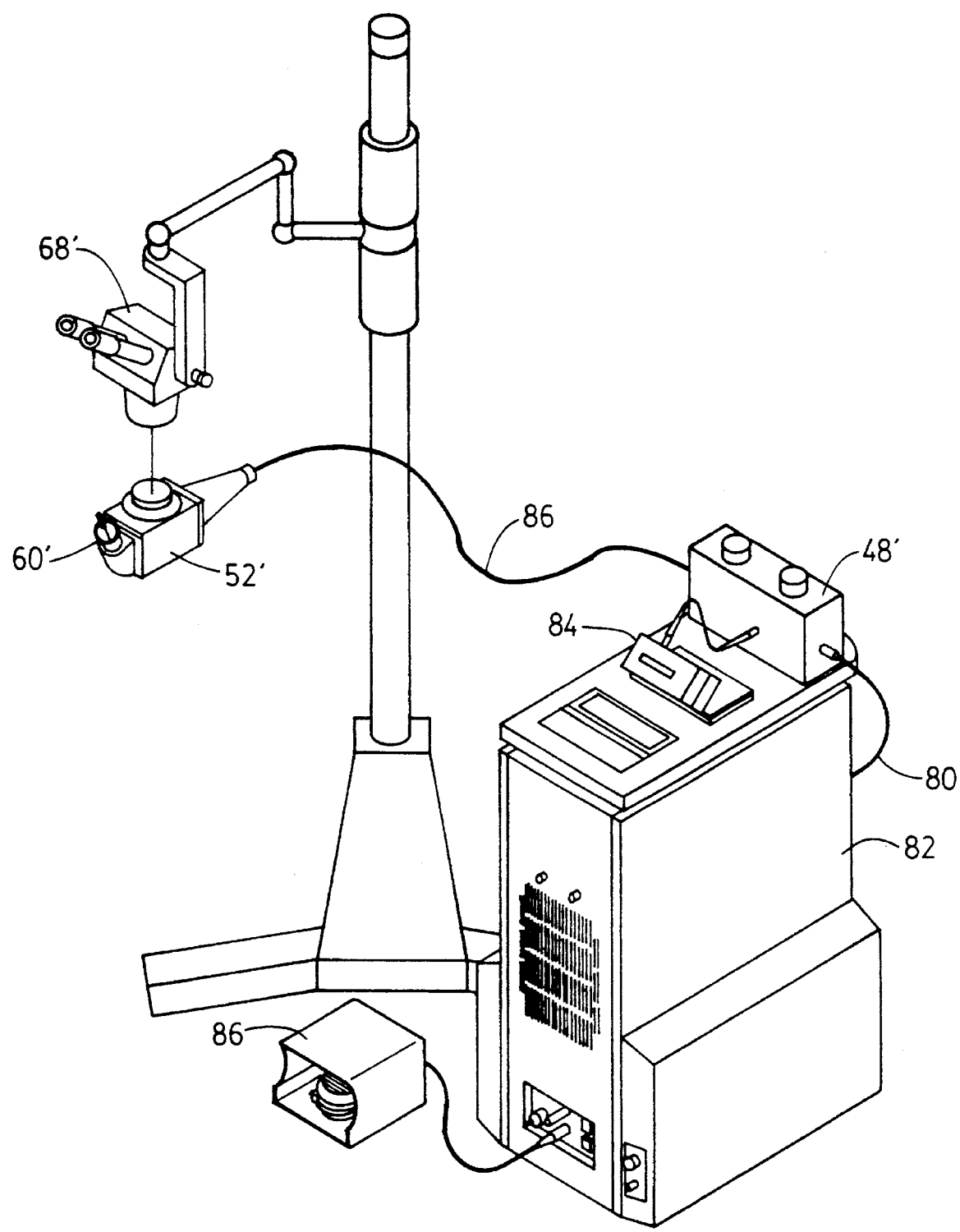
FIG._5.

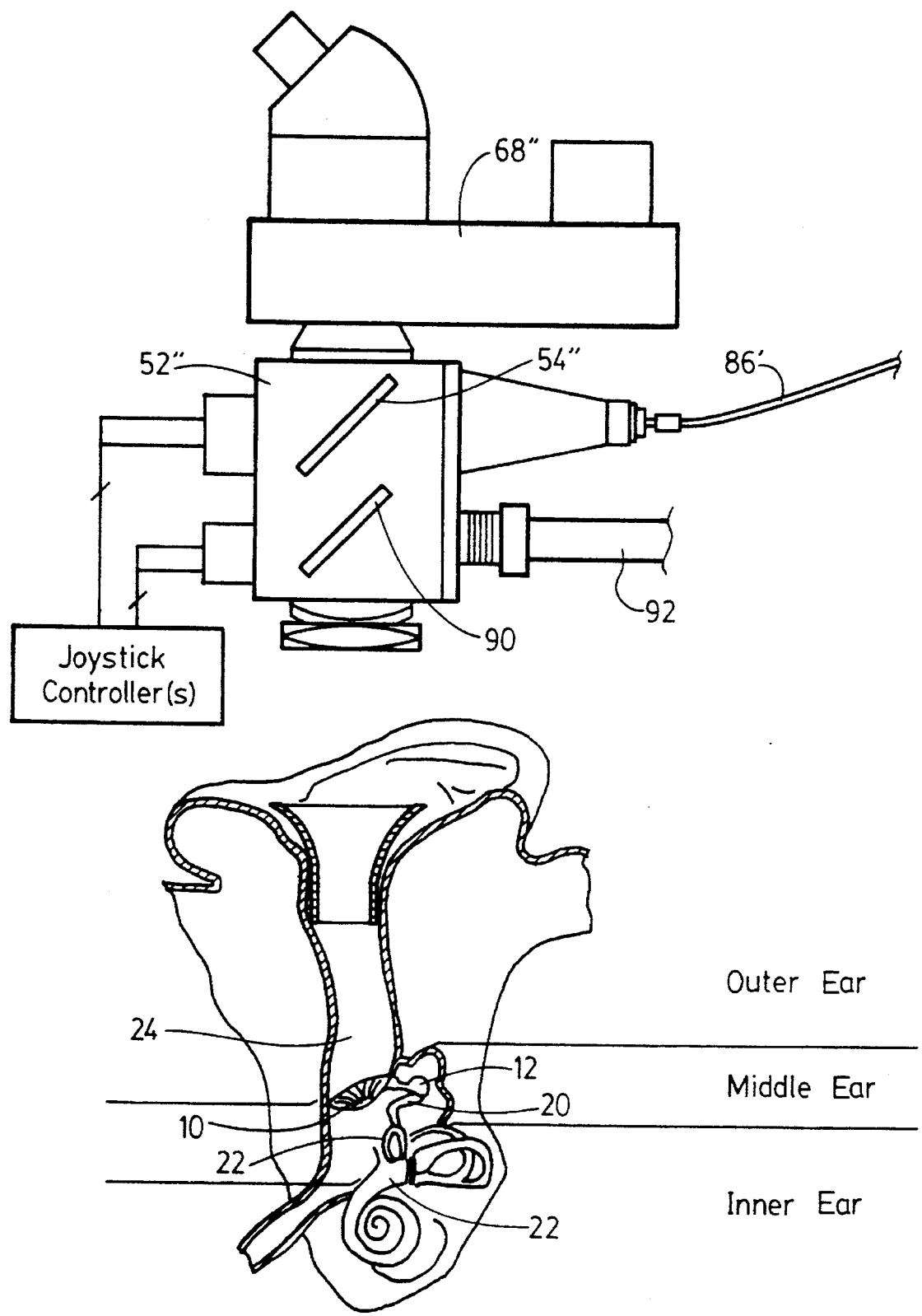
FIG._6.

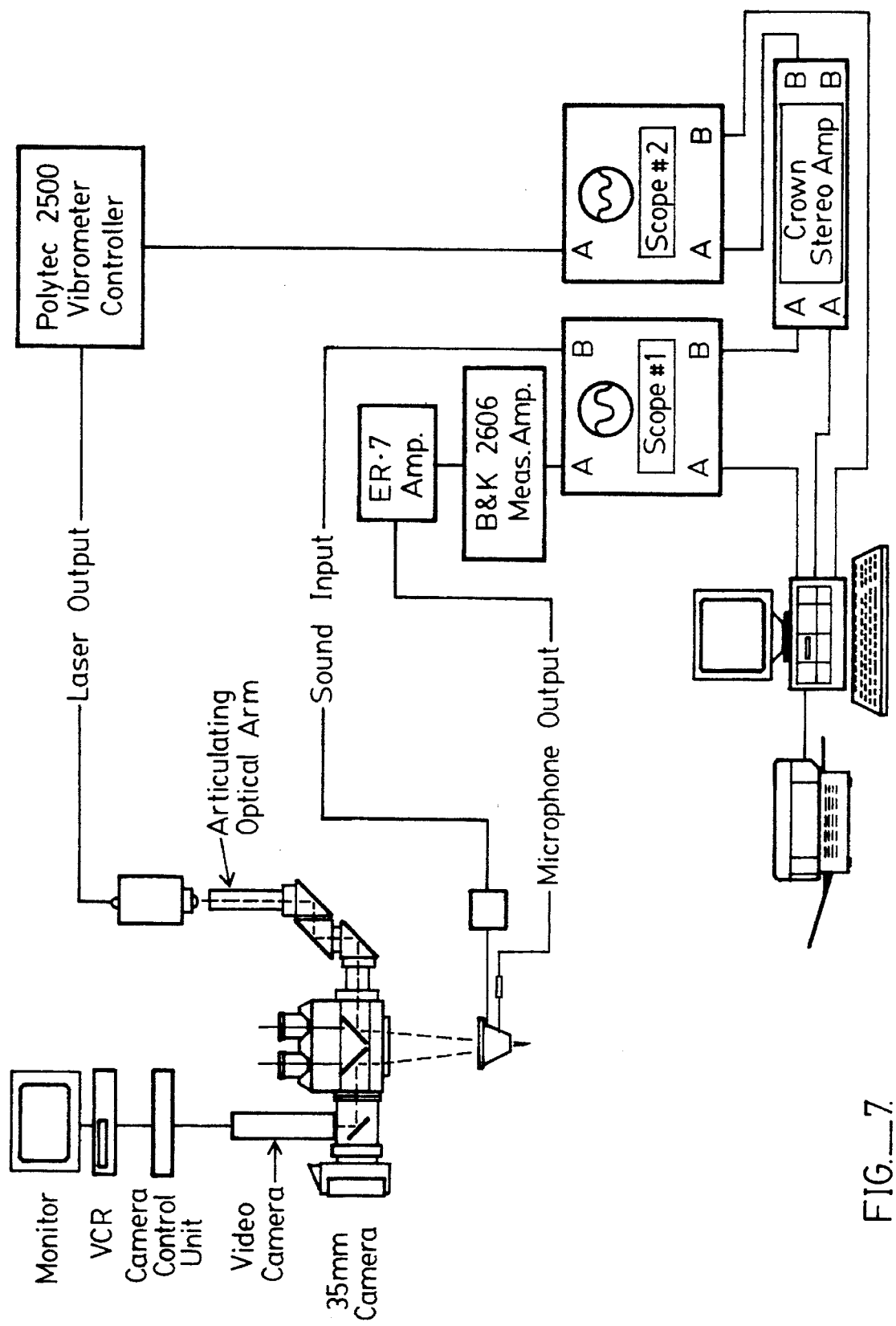
FIG.—7.

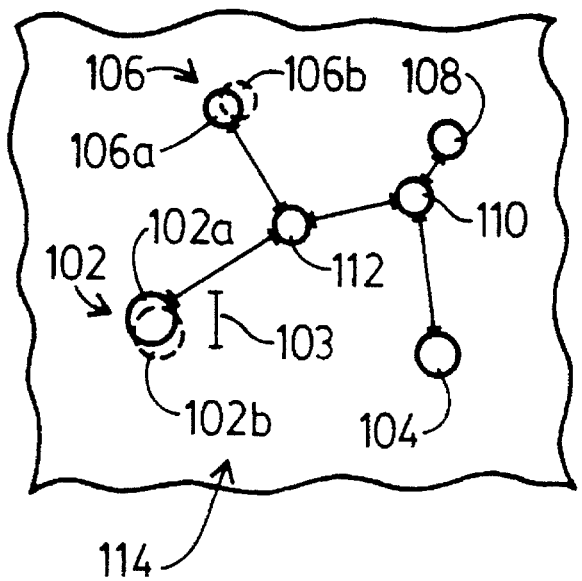
FIG._9.
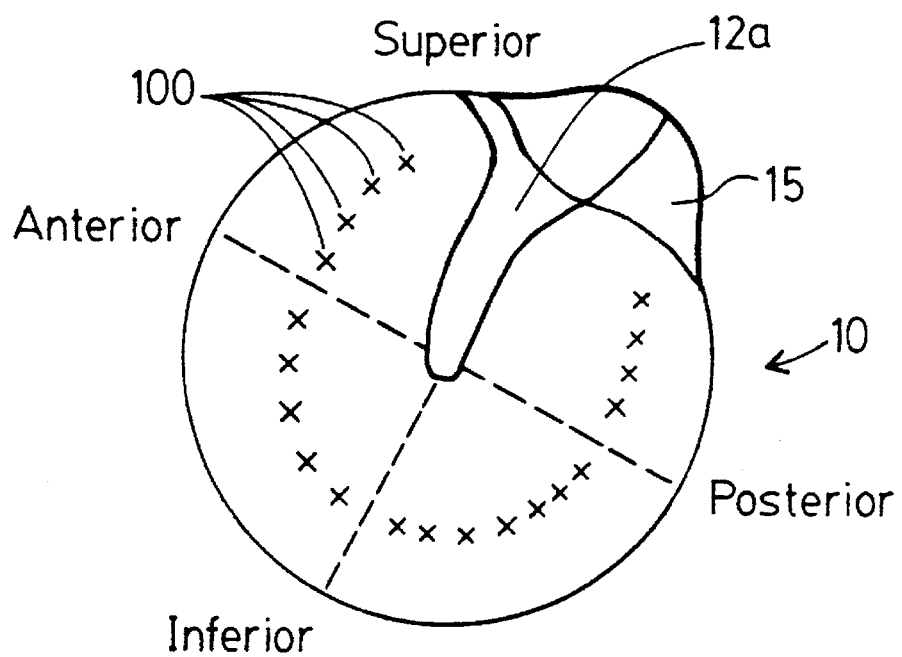
FIG._8.

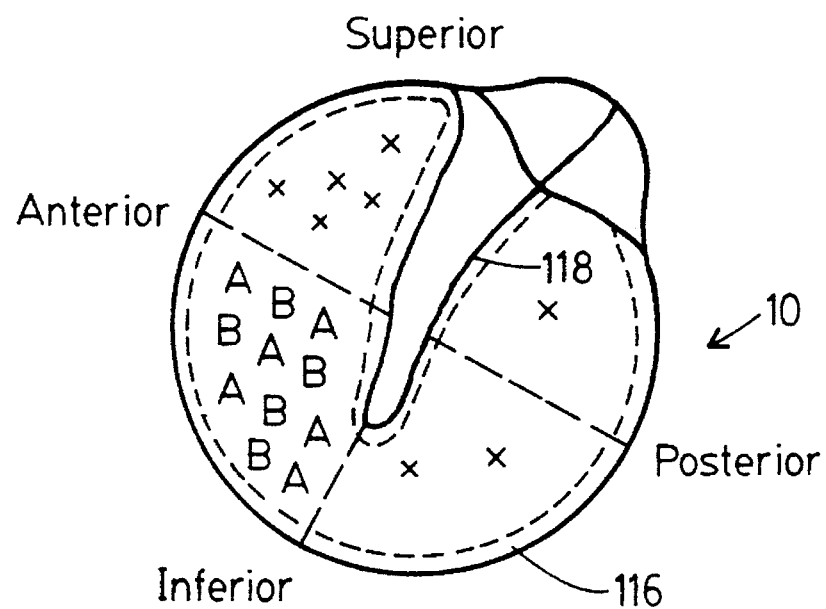
FIG._10.
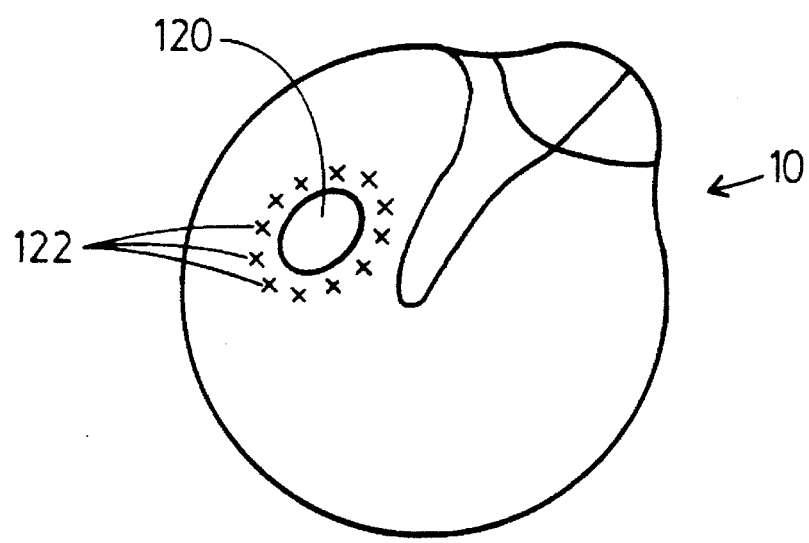
FIG._11.

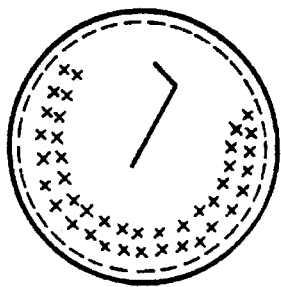
Outer ⅓
FIG._12A.
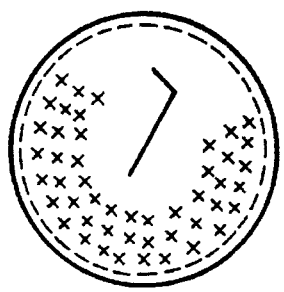
Outer ⅓
FIG._12B.
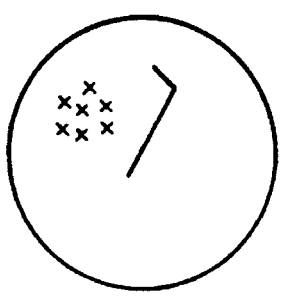
FIG._12C.
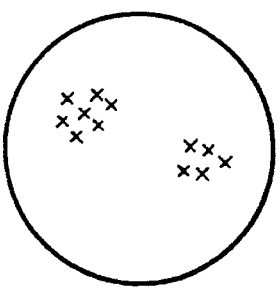
FIG._12D.
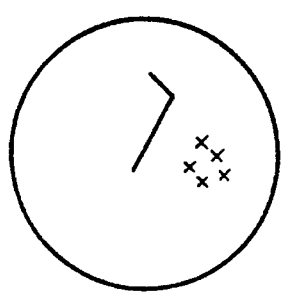
FIG._12E.
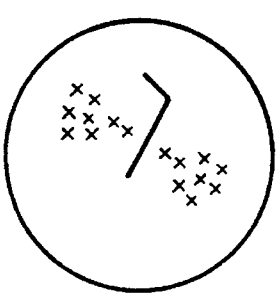
butterfly
FIG._12F.
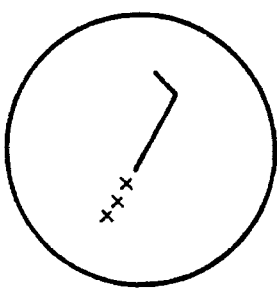
extending manubrium
FIG._12G.
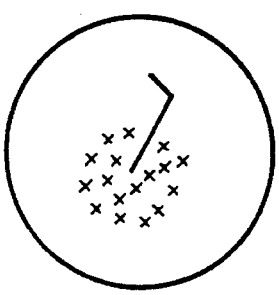
inner ½
FIG._12H.
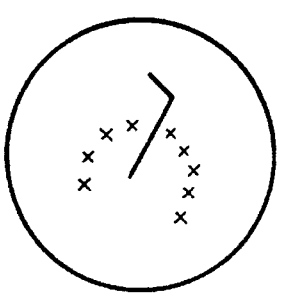
center between umbo + annulus except for inferior ⅓
FIG._12I.

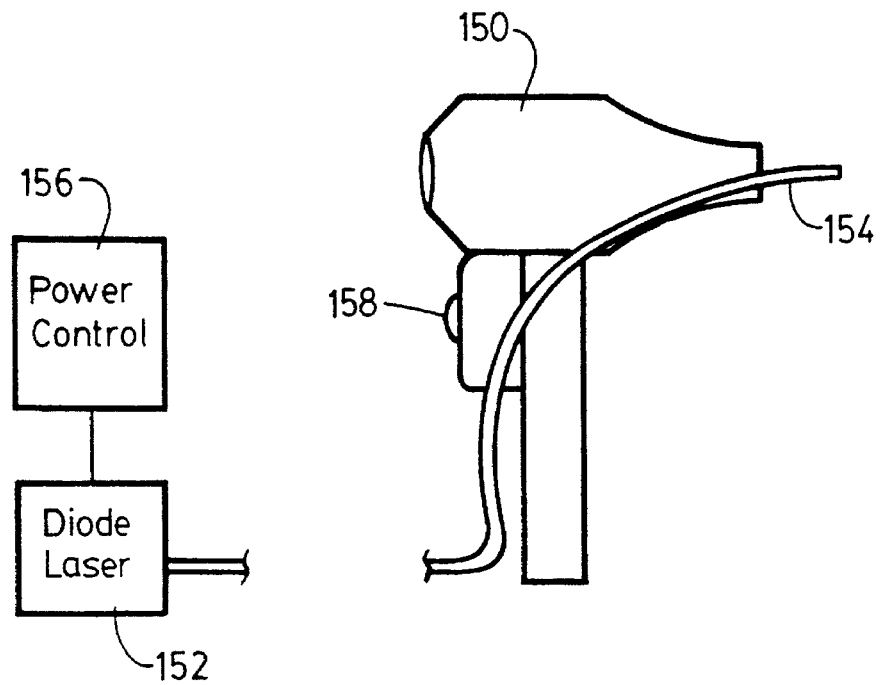
FIG._13.
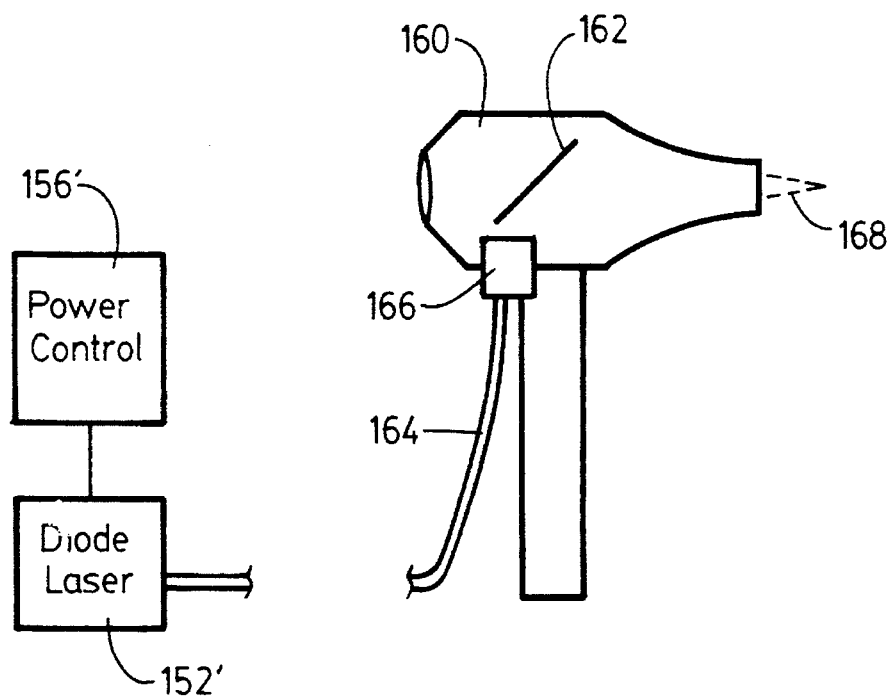
FIG._14.

METHOD AND APPARATUS FOR TYMPANIC MEMBRANE SHRINKAGE

BACKGROUND OF THE INVENTION

The present invention relates to a method and apparatus for improving human hearing.

A common hearing problem involves the tympanic membrane of the middle ear. Sound pressure in the air is translated into pressure in the cochlea fluids of the inner ear through the tympanic membrane and the ossicular chain (the malleus, incus, and stapes) of the middle ear. When the tympanic membrane vibrates, the ossicular chain pushes on the oval window membrane of the cochlea to move the fluids of the inner ear. Because the inner-ear fluid is denser than air, sounds in the air would not be very efficient in directly moving the fluid. The fluid has a higher characteristic impedance than the air. The impedance mismatch means that more pressure is required for a stimulus to be propagated in the cochlear fluids than in air.

When stimulated by high sound pressure levels, the tympanic membrane operates as a stretched membrane, and portions of the air pressures acting on it are transferred to the manubrium of the malleus. About two-thirds of the tympanic membrane total area (typically about 55 mm$^2$ of the total 85 mm2 area) is stiffly connected to the manubrium and thus vibrates at high levels. The stapes makes contact with the oval window and fluids of the inner ear. The area of the stapes footplate is about 3.2 mm$^2$. Since the area of the stapes footplate into the inner ear is considerably smaller than the effective area of the tympanic membrane, the difference in surface area acts to increase the pressure exerted on the cochlea. The pressure transformation from the tympanic membrane to the inner ear depends upon the frequency of the acoustic stimulus.

A common hearing problem is caused by the loosening of the tympanic membrane. This loosening can be caused by heredity, a puncture in the tympanic membrane, some surgical procedures, loud noises, or aging. This loosening may shift the resonant frequency of the middle ear to a lower frequency and/or decrease efficiency of the middle ear structures, both of which can cause a hearing loss in the range of 1 kHz to 6 kHz, which is a crucial one for the hearing of human voices.

To avoid this problem, hearing aids are typically used to amplify sounds in the range of 1 kHz to 6 kHz. Alternately, a passive filter can be used to filter out some of the sounds in the lower frequency range so that voices do not seem as muffled. A problem with these devices is that people generally do not like to use them for comfort and cosmetic reasons.

It is desired to have an improved method for improving the hearing in the range of from 1 kHz to 6 kHz.

SUMMARY OF THE INVENTION

The present invention involves tightening of the tympanic membrane by shrinking portions of the collagen matrix layer in the tympanic membrane. By tightening the tympanic membrane, the pressure gain of the middle ear structures can be improved, particularly in the frequency range of 1 kHz to 6 kHz. This improvement may be caused by a shifting of the resonant frequency response of the tympanic membrane to a higher frequency and/or improvement in efficiency of the tympanic membrane.

The shrinking effect is caused by raising the temperature of portions of the collagen layer to temperatures in the range of 60° C. to 70° C. This temperature raise causes the collagen in that portion to shrink, and thus causes the remaining portions of the tympanic membrane to be tightened. Energy, such as laser light, can be supplied to portions of the collagen membrane to raise the temperature of these portions.

The energy supplied to the collagen layer should preferably not form holes in the tympanic membrane by ablation. This method is different from some prior art laser treatments to the tympanic membrane, such as a myringotomy, which form holes in the tympanic membrane by ablation.

Additionally, the spot size, intensities, and frequencies of uses of the supplied energy should preferably be such that the temperature rise of the portion of the collagen layer does not cause acute inflammation of the tympanic membrane. Inflammation of the tympanic membrane can result in the replacement of the collagen in the collagen matrix, and thereby return the tympanic membrane to its previous shape.

The energy used to raise the temperature of the collagen layer is preferably within a range of frequency values such that the energy can raise the temperature of the collagen layer without ablation. The frequencies of some lasers, such as $CO_2$ lasers, are very highly absorbed by collagen, and thus the energy is absorbed in a thin top layer of the material which is ablated. For this reason, $CO_2$ lasers are used for treatments such as myringotomies, in which holes are formed in the tympanic membrane. Energies that use too low a frequency will not be sufficiently absorbed by the collagen layer. In this case, much more energy will be absorbed by the rest of the head than the collagen layer itself.

A frequency range of 1.4 to 2.6 microns gives an absorption range of about 10 to 150 cm$^{-1}$ in the collagen matrix layer. This range is preferable for the present invention. A narrower range of 1.8 to 2.55 microns is more preferable, and the range of 2.0 to 2.2 microns has the advantage that this range includes the frequencies of holmium:YAG and holmium:YLF lasers. These holmium lasers are relatively economical.

The powers used to heat the collagen matrix layer are relatively low, due to the thinness of the collagen matrix layer in the tympanic membrane. Preferably, energies of four to twenty joules per cm$^2$ can be used. Beam spot widths of 0.3 to 1.5 millimeters are preferably used to irradiate portions of the tympanic membrane. Pulse trains of 0.5 to 1 seconds long at 5 to 10 Hz can be used.

Patterns of spots irradiated on the tympanic membrane should preferably have the spots separated from their nearest neighboring spot by a sufficient distance such that an adequate unshrunken portion remains. This distance is preferably an average distance of at least one beam spot width. The remaining unshrunken portions are stretched by the shrinking of collagen in the area of the spots.

A relatively large amount of the energy may pass through the tympanic membrane. If the energy wavelength were adjusted so that substantially all the energy was absorbed by the tympanic membrane, ablation may occur. For this reason, the irradiation of the spots should preferably avoid the portions of membrane directly in front of the manubrium. Since the manubrium is part of the tympanic membrane, the energy would be heavily absorbed by the bone if the energy was directed to portions of the tympanic membrane directly in front of or near the manubrium. Since the other ear structures are further away from the tympanic membrane, only relatively diffuse energy impacts these structures when the tympanic membrane is irradiated.

The pattern of spots should also preferably avoid the par flaccida portion of the tympanic membrane. Tests have shown that this portion of the tympanic membrane does not respond well to the present type of irradiation treatment. This may be caused by a lack of a collagen layer on this portion of the tympanic membrane. One useful pattern of spots is a horseshoe pattern avoiding the manubrium and pars flaccida.

Irradiating portions of the tympanic membrane near the connection of the tympanic membrane and the ear canal also has less of an effect, either because the tympanic membrane is thicker in this area, or because less of the membrane is stretched by the shrinking.

The irradiation of spots on areas of the tympanic membrane, other than the pars flaccida, that appear loose is another effective strategy. These portions can be found visually using an otoscope, an operating microscope or with the use of a vibrometer. The vibrometer can be used to determine the frequency response of the tympanic membrane to find the loose portions. The vibrometer can also be used to test whether the treatment is effective in specific portions.

Retraction pockets on the tympanic membrane can also be treated. Energy is directed in a pattern around the retraction pocket to tighten this retraction pocket. The retraction pocket itself is preferably not irradiated, since this area may not have a collagen layer. This treatment may improve hearing in a lower frequency range from 0.2 kHz to 1 kHz.

Additionally, a low-power visible laser can be used in conjunction with an infrared laser. The low-power visible laser can be placed with its beam focused on the position that will be irradiated by the shrinking energy of the infrared laser. The operator can use the visible laser to target the infrared laser. An optical fiber can be used to help maintain the co-planarity of the lasers.

An operating microscope can be used with the energy delivery system. A partially-reflective dichroic mirror is used to allow some visible light to pass through so that the ear can be seen with the operating microscope. The partially-reflective dichroic mirror also reflects some of the visible light onto the tympanic membrane so that the visible laser can produce a spot on the tympanic membrane, as well as reflecting the energy from the infrared laser to this spot.

Another embodiment of the present invention involves the use of a continuous wave (CW) diode laser to tighten the tympanic membrane. A laser diode that emits continuous radiation in the range 1.9 to 2.1 microns can be used to tighten the tympanic membrane. The diode energy can be coupled into an optical fiber and delivered to the tympanic membrane. Systems using laser diodes, optical fibers and otoscopes are inexpensive, and do not require an operating microscope.

BRIEF DESCRIPTION OF THE DRAWINGS

The above and other features of the present invention will become more apparent upon reading the following detailed description in conjunction with the accompanying drawings, in which:

FIG. 1 is a graph illustrating the frequency dependance of the displacement of the tympanic membrane for sounds;

FIG. 2A is a front view of the right tympanic membrane;

FIG. 2B is a side cross-sectional view of the tympanic membrane FIG. 2A;

FIG. 2C is a side cross-sectional view of a portion of FIG. 2B showing the collagen matrix layer;

FIG. 3 is a graph showing the absorption coefficient of water in $cm^{-1}$ versus wavelength;

FIG. 4 is a diagram of the ear treatment system;

FIG. 5 is a perspective view of the ear treatment system of FIG. 4;

FIG. 6 is a diagram of an alternate embodiment of the ear treatment system, which also shows a cross-section of a human ear;

FIG. 7 is a diagram of a vibrometer;

FIG. 8 is a diagram of the tympanic membrane showing locations of spots to be irradiated;

FIG. 9 is a diagram of a pattern of spots irradiated on a portion of a tympanic membrane;

FIG. 10 is a diagram of the tympanic membrane showing an alternate pattern of spots to be irradiated;

FIG. 11 is a diagram of the tympanic membrane showing a depression surrounded by irradiated spots;

FIGS. 12A–I are diagrams showing alternate patterns of spots on the tympanic membrane;

FIG. 13 is a diagram showing an otoscope along with laser diode and optical fiber probe used to deliver energy to the tympanic membrane; and FIG. 14 is a diagram showing an otoscope with a beamsplitter, laser diode and optical fiber used to deliver energy to the tympanic membrane.

DETAILED DESCRIPTION OF THE DRAWINGS

FIGS. 2A–2C are diagrams of the tympanic membrane. FIG. 2A is a front view of the right tympanic membrane 10. The tympanic membrane contacts the manubrium 12a of the malleus shown in FIG. 2B. The pars flaccida 15 is the portion of the tympanic membrane that is normally loosely connected to the ear canal, and does not act as a stretched membrane. The other portion of the tympanic membrane is called the pars tensa. As can be seen from the side view of FIG. 2B, the tympanic membrane is essentially cone-shaped, with the umbo 16 at the center. FIG. 2C shows the layers of the tympanic membrane. The tympanic membrane is about 0.1–0.2 mm thick with about two-thirds of this thickness contributed by the middle collagen matrix layer 18b. Surrounding the middle collagen matrix layer 18b is an inner epidermal layer 18c and an outer epidermal layer 18a. A layer (not shown) of mucous is on the inner epidermal layer 18c. The central collagen matrix layer 18b shrinks when the temperature of the collagen layer is raised to the range of about 60° to 70° C. This shrinking causes tightening of the tympanic membrane.

FIG. 6 shows a cross-sectional view of the ear. The tympanic membrane 10 is connected to the ossicular chain comprising the malleus 12', the incus 20, and the stapes 22. The ossicular chain connects the tympanic membrane 10 to the cochlea 22 of the inner ear. Outer ear structures shown include the ear canal 24.

FIG. 1 is a graph illustrating the frequency dependance of the displacement of the tympanic membrane for sounds. The displacement for a given frequency is related to the pressure gain for the middle ear structure at that frequency. This displacement is related to the pressure gain in the middle ear structures. Line 30 shows the curve for an average human ear. Note that the curve peaks at about 1 kHz and has a 9 dB per octave drop afterwards. A flaccid tympanic membrane may cause the resonant frequency to shift lower, as shown in line 33. Line 33 shows a curve that has a peak at 500 kHz.

Note that, even though the peaks of curves 33 and 30 are shown at the same level, over the important range of 1 kHz to 6 kHz the curve 33 is substantially less than the average curve 30. It is also likely that the peak of the curve 33 of the loose tympanic membrane would be less than the average curve 30. The tightening of the tympanic membrane can shift the frequency response of the tympanic membrane up to a 1 kHz peak, which improves the frequency response over the 1 kHz to 6 kHz range. Line 34 shows the response for a tympanic membrane that has its resonant frequency shifted to 3 kHz. Note that the shift for line 34 may reduce the hearing at the lower frequencies, e.g. around 500 kHz, but the hearing in the crucial 1 kHz to 6 kHz is range is improved.

Line 31 shows the frequency response curve that is one standard deviation below average, and line 32 shows the frequency response curve that is one standard deviation above average. A benefit of the present treatment method is that people with hearing that is a standard deviation below average can have their hearing improved. People whose hearing is a standard deviation below average may have "normal" hearing. In fact, the lower-than-average frequency response of the middle ear of curve 31 might not be determined by the standard test for middle ear hearing loss. In the standard test for middle ear hearing loss, a vibrator is put next to bones in the patient's head so that sound directly travels to the inner ear, bypassing the middle ear structures. The perceived loudness of this vibrator's tone is compared to the perceived loudness of an aural tone. The aural tone is calibrated such that people with average hearing perceive the two tones as having equal loudness. People who have hearing found to be borderline normal or abnormal using this test may have their hearing improved by the treatment of the present invention.

A more accurate way of testing for middle ear hearing loss that may be improved by the present invention is the use of an impedance test. In an impedance test, the intensity and phase of a reflected tone is compared to the intensity and phase of the tone sent into the ear. A test using normal air pressures is done; then the test is repeated with positive air pressure pumped into the ear canal. The positive pressure pumped into the ear canal tightens the tympanic membrane if it is loose, so that the results of the two tests can be used to determine if the tympanic membrane is loose.

Ideally, the present invention may allow for the production of an improved frequency response like in curve 32. Line 35 shows a curve for a tympanic membrane that is overly tightened and has a poor frequency response. Overtightening can be avoided by using a vibrometer to test the frequency response during the treatment, or by not irradiating a large number of spots on the tympanic membrane.

In addition, treatment with energy may improve the hearing in the range 200 kHz to 1 kHz. This effect is noticeable for people who have a depression or retraction pocket on the tympanic membrane. People with a depression or a retraction pocket on the tympanic membrane tend to have poor hearing all over the range 0.2 to 6 kHz. The treatment shown with respect to FIG. 11, and discussed below, particularly improves the hearing in the low frequency (200 hz to 1 kHz) range.

FIG. 3 is a graph of the absorption coefficient versus wavelength for water. The middle collagen matrix layer of the tympanic membrane is comprised mostly of water. It is desired to have the absorption such that the laser light is absorbed by the collagen layer, but is not so strongly absorbed that ablation damage occurs. Prior art laser systems used to treat the ear have lasers with a frequency that is highly absorbed by water, such as $CO_2$ lasers. These systems are used for ablation in myringotomy procedures.

Additionally, energy with too low an absorption coefficient may not effectively heat the collagen. This would require a very high level of energy in order for the desired temperature raise to occur in the tympanic membrane.

In a preferred embodiment, the frequency range of the supplied energy is from 1.4 to 2.6 microns, which corresponds to an absorption range of about 10 to 150 $cm^{-1}$. This is a wider range than is used for the shrinkage of collagen in eye surgery. The energies and pulses are adjusted to avoid damage to the collagen due to ablation. The radiation is sent in ½ to 1 second long pulse trains of 5 to 10 kHz. The spot size on the tympanic membrane ranges from 300 to 1500 microns. Energies range from 4 to 20 joules/$cm^2$. The thinness of the collagen layer requires these low energies. Since the tympanic membrane is a thin layer surrounded by air, energy absorbed by the tympanic membrane cannot be effectively transferred to other body structures. Additionally, temperatures above 70° C. may cause an acute inflammatory response which may result in an unwanted reversal of the membrane shrinkage.

FIGS. 8–12 show different patterns of irradiated spots on the tympanic membrane. FIG. 8 is a diagram of the tympanic membrane 10 showing locations of spots 100 to be irradiated. In the treatment, the eardrum area should be numbed with a local anesthetic, such as topical xylocaine. The irradiation of the spots should preferably avoid the portions of membrane directly in front of the manubrium 12a, since some of the supplied energy will pass through the tympanic membrane. Because the manubrium 12a is directly behind the portions of the tympanic membrane, the manubrium could absorb a large amount of radiation. Other structures in the ear may receive energy when different spots are irradiated, but this energy will not be as concentrated, so there is much less risk of damage.

The pattern of spots should also preferably avoid the par flaccida 15 of the tympanic membrane 10. Tests have shown that the pars flaccida 15 does not effectively tighten due to the irradiation of energy. The pars flaccida 15 may lack a collagen layer which can shrink in spots to tighten this portion.

One useful pattern for tightening the tympanic membrane is the horseshoe pattern of spots 100 shown in FIG. 8. This horseshoe pattern avoids the par flaccida 15 and the portion of the tympanic membrane in front of the manubrium 12a.

FIG. 9 is a diagram of a pattern of spots 102, 104, 106, 108, 110, 112 irradiated on a portion of a tympanic membrane 114. Patterns of spots irradiated on the tympanic membrane preferably should have the spots separated from their nearest neighboring spot by a sufficient distance such that an adequate unshrunken portion remains. The unshrunken portion should be such that it supports the stretching of the tympanic membrane.

The distance between nearest neighbor spots is preferably an average distance of at least one beam spot width. Note that this average distance condition may still be met if some of the spots, such as spots 110 and 108, are less than a one beam spot width from each other.

Additionally, the same spot may be irradiated more than once. The first irradiation may be done with relatively low power. If no shrinking is noticed, more power could be used for the next irradiation at the same spot. Of course, it is likely that the first and any further irradiation will be at least slightly out of alignment. Note that the first irradiation 102a does not completely overlap the second irradiation 102b. The spot 102 should be considered as the combined areas of the two irradiations 102a and 102b. The "beam spot width" for spot 102 should be defined as the longest distance containing both irradiation 102a and 102b shown as length 103.

FIG. 10 is a diagram of the tympanic membrane 10 showing an alternate pattern of spots to be irradiated. This pattern has its spots (marked as A's, B's, and X's) concentrated on the anterior, or front, portion of the tympanic membrane. This portion has been most responsive to the irradiation treatment in tests.

The pattern of spots preferably avoids irradiating an area 116 that is within one-half a millimeter from the edge of the tympanic membrane at connection of membrane to ear cavity. The irradiation treatment is less effective in this area, either because of the thickness of the tympanic membrane in this area, or because the connection of the tympanic membrane to the ear canal inhibits the stretching effect. The pattern of spots irradiated in the irradiation step also avoids irradiating an area 118 that is 0.1 millimeters from the connection of the tympanic membrane to the manubrium 12a.

One method of forming a pattern on the tympanic membrane involves supplying energy to spots on areas of the tympanic membrane, other than the pars flaccida, that appear loose. The portions can be found visually using an otoscope, an operating microscope or with the use of a vibrometer. The vibrometer can be used to determine the frequency response of the tympanic membrane to find the loose portions. A frequency response mapping for the ear can be compared with a mapping for an average ear to find the loose sections. The vibrometer can also be used to test whether the treatment is effective in tightening specific portions. Alternately, a probe could be used to test the Young's modulus or other elastic characteristics of the tympanic membrane to find loose portions.

One way of tightening a portion of the membrane is shown with respect to FIG. 10. A first series of spots, such as the spots labeled "A," can first be irradiated by the system to shrink the membrane. These "A" spots are relatively evenly dispersed over the portion of the tympanic membrane that it is desired to be tightened. The portion to be tightened is shown as the anterior inferior quadrant. After the "A" spots are irradiated by the system, the frequency response of the portion can be examined with a vibrometer. If the frequency response is good, no more spots need be irradiated. If the frequency response is still poor, additional spots "B" can be irradiated such that the "B" spots interleave with the "A" spots. Note that the combined group of both the "A" and "B" spots is also relatively evenly distributed over the portion to be tightened.

FIG. 11 is a diagram of the tympanic membrane 10 showing a depression 120 surrounded by irradiated spots 122. The depression 120 on the tympanic membrane can typically be visually spotted through an otoscope or an operating microscope. In addition to impeding hearing, the depressions can provide a pool for water and/or prevent the self-cleaning of the ear, which may cause infections. One prior way to remove the depressions involved surgery to place a graft material behind the depression to stiffen the tympanic membrane. This surgical method adds mass to the tympanic membrane, which can affect the membrane's frequency response, and is a relatively complicated procedure. In the irradiation method, the depression is surrounded by spots to pull the membrane in the depression tighter. Spots are not irradiated directly on the depression, since the depression might not include a collagen layer. Fluid may be added to the inner ear before the treatment to insure that the depression is not abnormally attached to middle ear structures, so that the membrane will not be torn because of the shrinking. The irradiation of patterns of spots about the about the retraction pocket may have the effect that low-frequency hearing in the range 0.2 to 1 kHz is improved.

FIGS. 12A–I are diagrams showing alternate patterns of spots on the tympanic membrane. These patterns are used for tightening the tympanic membrane. For all of the patterns discussed above, repetition of the treatment may be necessary. This may comprise treating the ear every few years, or may comprise re-treating the ear a week after the first treatment.

FIG. 4 shows a diagram of an ear treatment system 40. This system uses an infrared laser 42 such as a holmium:YAG or holmium:YLF laser. This laser is coupled to optics 44 into a fiber optic cable 46. The energy is then sent through the energy attenuator 48, with its associated energy meter 50. The energy attenuator can reduce the energy of the infrared laser to the desired level. The energy is sent to the directing optics 52, which includes a dichroic mirror 54. The directing optics 52 directs the energy through the speculum 56 onto the tympanic membrane of the ear 58. A micromanipulator, such as a joystick controller 60, controls the X and Y adjustments of the dichroic mirror 54 so as to position the laser energy onto the tympanic membrane of the ear 58. Light from a visible laser 62 is combined with the energy from the infrared laser 42 using a mirror 65 and the dichroic mirror 66 onto the optical fiber 46. The dichroic mirror 66 reflects the visible laser light, but allows the infrared laser to transmit therethrough. Since the visible laser light is sent along with the infrared laser light in the fiber optic cable 46, the visible laser light will give an indication of the target of the infrared laser pulses.

Dichroic mirror 54 in the directing optics 52 reflects the infrared light from the infrared laser 42, but is partially transmissive for visible light. In this manner, the tympanic membrane can be seen through the dichroic mirror 54 with the operating microscope 68. The dichroic mirror 54 is also partially reflective for the visible light, so that the light from the visible laser 62 is partially reflected onto the tympanic membrane of the ear 58. In one embodiment, this dichroic mirror 54 is eighty percent reflective for 2.1 micron infrared laser energy, and greater than seventy percent transmissive for visible light.

Control of the infrared and visible lasers can be done by the control system 70 connected to input/output device 72. The control system 70 can keep the infrared laser 42 off until the desired spot is targeted by the visible laser 62.

FIG. 5 is a perspective view of the system of FIG. 4. This device uses a modified medical laser to form the ear-treating device of the present invention. A GLase 210 or SLase 210 available from Sunrise Technologies, Inc. of Fremont, Calif. can be modified to form the ear-treatment device. These devices are used for eye surgery, as described in Sand U.S. Pat. Nos. 4,976,709 and 5,137,530, which are incorporated herein by reference.

Accessory products that are added to the GLase 210 or SLase 210 in a preferred embodiment include a 300-micron diameter fiber optic cable 80, which connects the laser console 82 to the shutter-attenuator control box 48'. The shutter-attenuator box 48' sits on top of the laser console 82 and contains a manual attenuator adjustment to adjust the energy levels of the infrared laser being sent to the tympanic membrane, and an energy monitor beam-splitter and detector, as well as a manual safety shutter. The manual safety shutter can be used for calibrating the energy levels. The energy monitor display 84 can be used to monitor the energy level of the infrared laser energy. A 300-micron diameter fiber optic 86 connects the control box to an operating microscope delivery system 54'. The operating box delivery system 54' can be mounted to a standard operating-room microscope 68' that includes the micromanipulator 60'. This operating-room microscope can be, for example, a Zeiss OPMI. The foot pedal 86 can be used for controlling the operation of the infrared laser.

FIG. 6 is a diagram showing an alternate embodiment of the delivery system of the ear treatment system of the present invention. The delivery system 52' includes the dichroic mirror 54". Also shown is an additional dichroic mirror 90, which can be used to reflect the beam directed through the articulated arm 92, but transmit the infrared invisible light from the cable 86', which is reflected off the dichroic mirror 54". In this manner, a vibrometer (not shown) can be connected to the device for determining the frequency response of the tympanic membrane 10. Also shown in this diagram is a cross-sectional view of the ear structure showing the outer, middle and inner ear.

FIG. 7 shows a vibrometer which is used to determine the frequency response of the tympanic membrane. The vibrometer is focused on different portions of the tympanic membrane. The reflections off of the tympanic membrane for different input sounds can be determined by using a laser beam which measures the displacement of the tympanic membrane for the sound input. In this manner, the frequency response of the tympanic membrane can be mapped.

Another embodiment of the present invention includes the use of a continuous wave (CW) diode laser to tighten the tympanic membrane. A laser diode that emits continuous radiation in the range 1.9 to 2.1 microns can be used. A CW laser diode with output frequencies in this range has the advantage that these output frequencies have a higher absorption coefficient for collagen than the holmium wavelength. More importantly, the wavelength can be selected at a frequency in that range and a diode made with the desired output. In this way, an optimum wavelength for the structure and geometry of the ear can be chosen. The diode laser can run continuously or for as long as desired, thus eliminating the very short pulses of the Holmium laser, which may cause shock waves. These shock waves should be avoided, both for the comfort of the patient, and also to avoid possible disruption of the collagen fibers at the exposure sights on the ear drum.

Diode lasers are compact, can be operated with accurate electronic control, and the emitted radiation can be introduced into an optical fiber easily with little loss. The diode laser can be substituted for the holmium laser in the embodiment discussed above.

Alternately, simpler delivery systems could be used with an otoscope. An otoscope is an instrument that is typically used to view the outer ear and tympanic membrane. FIG. 13 is a diagram showing an otoscope 150 along with laser diode 152 and optical fiber probe 154 used to deliver energy to the tympanic membrane. The laser diode 152 is controlled by the power control circuitry 156 and supplies energy along the optical fiber probe 154 to the tympanic membrane. Probe 154 is used to contact the desired portions of the tympanic membrane. Manipulator 158 can be used to position the fiber probe 154. The probe 154 can be retracted when it is not needed.

FIG. 14 is a diagram showing an otoscope 160 with a beam-splitter 162, laser diode 152', and optical fiber 164, used to deliver energy to the tympanic membrane. In this embodiment, the laser energy in the optical fiber 164 is focused with optics 166 and reflects off the beam-splitter 162 out of the front of the otoscope 160. The tympanic membrane can be viewed by the operator through the beam-splitter 162, since the beam-splitter 162 allows at least some visible light to pass through. The focused beam 168 can be directed by moving the otoscope 160. In another embodiment, the beamsplitter 162 can be adjusted to direct the output beam.

Advantages of the systems shown in FIGS. 13 and 14 include lower cost and ease of administration. These embodiments also do not require an operating microscope. The systems shown in FIGS. 13 and 14 can be used to irradiate the patterns of spots shown in FIGS. 8–12. The spots are preferably irradiated with continuous energy in the range of 1 to 10 joules per $cm^2$. This energy can be lower than the energy used for the Holmium laser, since the laser diode preferably has a higher absorption coefficient in collagen. The spots are preferably irradiated with continuous energy for 0.01 to 0.5 seconds.

Various details of the implementation and method are merely illustrative of the invention. It will be understood that various changes of details may be within the scope of the invention, which is to be limited only by the appended claims.

What is claimed is:

1. A method for treating the ear comprising supplying energy to a tympanic membrane, the energy having a collagen absorption coefficient in a range of 10 to 1 50 $cm^{-1}$, to shrink collagen tissue in the tympanic membrane without damaging the tympanic membrane due to ablation of a portion of the tympanic membrane, wherein the tympanic membrane being treated has a retraction pocket, and the energy is directed in a pattern around the retraction pocket to tighten this retraction pocket.

2. The method of claim 1, wherein the irradiating step includes shrinking the collagen tissue of the tympanic membrane sufficiently to improve the frequency response of the tympanic membrane over at least part of the frequency range from 0.2 kHz to 6 kHz.

3. The method of claim 2, wherein the irradiating step includes shrinking the collagen tissue of the tympanic membrane sufficiently to improve the frequency response of the tympanic membrane over at least part of the frequency range from 0.2 kHz to 1 kHz.

4. A method for treating the ear comprising irradiating the tympanic membrane with energy, the energy having a collagen absorption coefficient in a range of 10 to 150 $cm^{-1}$, to shrink collagen tissue in a tympanic membrane without damaging the tympanic membrane due to ablation of a portion of the tympanic membrane, the method involving irradiating a pattern of different spots on the tympanic membrane, said spots having an average beam width in a range of 0.3 to 1.5 millimeters, wherein the spots are separated from their nearest neighboring spot by an average distance of at least one average beam spot width so that a sufficient matrix of unshrunken portions of the tympanic membranes collagen layer remain, the pattern being such that a smaller portion per unit area of a section of the tympanic membrane in front of a manubrium is irradiated with the energy than a remaining pars tensa sections of the tympanic membrane so that damage to the manubrium is avoided, and wherein said pattern of spots are such that the shrinking of the collagen tissue of the tympanic membrane is sufficient to improve a frequency response of the tympanic membrane over at least part of a frequency range from 1 kHz to 6 kHz.

5. The method of claim 4, wherein the irradiating step is such that the pattern of spots irradiated in the irradiation step avoids irradiating an area 0.5 millimeters from edge of the tympanic membrane at connection of membrane to ear cavity.

6. The method of claim 4, wherein the irradiating step includes irradiating energy in the range of 4–20 joules per $cm^2$.

7. The method of claim 4, wherein the irradiating step includes irradiating energy in the range of 1 to 10 joules per $cm^2$.

8. The method of claim 4, wherein the irradiating step includes irradiating the spots with a 0.5 to 1 second long pulse train at 5 to 10 kHz.

9. The method of claim 4, wherein the irradiating step includes irradiating the spots with continuous energy lasting 0.01 to 0.5 seconds.

10. The method of claim 4, further comprising the step of examining the frequency response of portions of the tympanic membrane to determine which sections of the pars tensa of the tympanic membrane are loose, and wherein the irradiating step includes irradiating these sections.

11. The method of claim 4, wherein the irradiation step comprises irradiating a anterior portion of the membrane more than a posterior portion.

12. The method of claim 4, wherein the irradiating step is such that the pattern includes four spots to two-hundred spots.

13. The method of claim 4, wherein the irradiating step is such that the pattern of spots irradiated in the irradiation step avoids irradiating the portions of membrane directly in front of the manubrium.

14. The method of claim 13, wherein the irradiating Step is such that the pattern of spots irradiated in the irradiation step avoids irradiating an area 0.1 millimeters from connection of the tympanic membrane to the manubrium.

15. The method of claim 4, wherein the irradiating step is such that the pattern of spots irradiated in the irradiation step avoids irradiating a pars flaccida portion of the tympanic membrane.

16. The method of claim 15, wherein the irradiating step is such that the pattern of spots is a horseshoe-shaped pattern.

17. The method of claim 4, wherein the irradiating step includes irradiating the spots in the pattern one at a time.

18. The method of claim 17, further comprising the step of examining the frequency response of portions of the tympanic membrane in between irradiating spots on the tympanic membrane so as to gain information about which parts of the tympanic membrane should be irradiated further.

19. A method for treating the ear comprising supplying energy to a tympanic membrane, the energy having a collagen absorption coefficient in a range of 10 to 150 $cm^{-1}$ to shrink collagen tissue in the tympanic membrane without damaging the tympanic membrane due to ablation of a portion of the tympanic membrane, wherein the shrinking of the collagen tissue of the tympanic membrane is sufficient to improve a frequency response of the tympanic membrane over at least part of a frequency range from 1 kHz to 6 kHz, the energy supplying step including irradiating a pattern of spots about a pars tensa portion of the tympanic membrane, said spots avoiding portions of the tympanic membrane directly in front of a manubrium.

20. The method of claim 19, wherein the energy supplying step includes supplying energy with a collagen absorption coefficient in a range of 15 to 120 $cm^{-1}$.

21. The method of claim 19, wherein the energy supplying step includes supplying energy in pulse trains 0.5 to 1.0 seconds in length at 5 to 10 kHz.

22. The method of claim 19, wherein the energy supplying step includes irradiating the spots with continuous energy for 0.01 to 0.5 seconds.

23. The method of claim 19, wherein the energy supplying step includes supplying energy to the tympanic membrane to shrink a collagen layer in this membrane with pulses of an infrared laser, and wherein the method further comprises indicating a target with a visible light laser.

24. The method of claim 19, wherein the energy supplying step includes contacting the tympanic membrane with a contact probe.

25. The method of claim 19, wherein the energy supplying step includes supplying a level of energy to the tympanic membrane which does not induce an acute inflammatory response.

26. The method of claim 19, wherein the energy supplying step includes shrinking the collagen tissue of the tympanic membrane sufficiently to improve the frequency response of the tympanic membrane over at least part of a frequency range from 1 kHz to 5 kHz.

27. The method of claim 26, wherein the energy supplying step includes shrinking the collagen tissue of the tympanic membrane sufficiently to improve the frequency response of the tympanic membrane over at least part of a frequency range from 1 kHz to 4 kHz.

28. A method for treating the ear comprising supplying energy to a tympanic membrane in wavelength range of 1.4 to 2.6 microns to shrink collagen tissue in the tympanic membrane without damaging the tympanic membrane due to ablation of a portion of the tympanic membrane, wherein the shrinking of the collagen tissue of the tympanic membrane is sufficient to improve a frequency response of the tympanic membrane over at least part of a frequency range from 1 kHz to 6 kHz, the tympanic membrane being treated has a retraction pocket, further comprising directing the energy in a pattern around this retraction pocket.

29. A method for treating the ear comprising supplying energy to a tympanic membrane in a wavelength range of 1.4 to 2.6 microns to shrink collagen tissue in the tympanic membrane without damaging the tympanic membrane due to ablation of a portion of the tympanic membrane, wherein the shrinking of the collagen tissue of the tympanic membrane is sufficient to improve a frequency response of the tympanic membrane over at least part of a frequency range from 1 kHz to 6 kHz, the energy supplying step includes irradiating a pattern of spots about the tympanic membrane with energy, said spots avoiding portions of the tympanic membrane directly in front of a manubrium.

30. The method of claim 1, wherein the energy supplying step includes irradiating the spots with pulse trains of 0.5 to 1.0 seconds in length.

31. The method of claim 1, wherein the energy supplying step includes irradiating the spots with continuous energy for 0.01 to 0.5 seconds.

32. The method of claim 1, wherein the energy supplying step includes supplying pulses of an infrared laser to the tympanic membrane, and wherein the method further comprises indicating a point of treatment with a visible light laser.

33. The method of claim 1, wherein the energy supplying step includes the step of contacting the tympanic membrane to supply energy with a contact probe.

34. The method of claim 1, further comprising the step detecting the frequency response of the tympanic membrane using a vibrometer.

35. The method of claim 1, wherein the energy supplying step includes maintaining the level of the energy supplied to the tympanic membrane below a level that would induce an acute inflammatory response.

36. The method of claim 29, wherein the energy supplying step includes shrinking the collagen tissue of the tympanic membrane sufficiently to improve the frequency response of the tympanic membrane over at least part of a frequency range from 1 kHz to 5 kHz.

37. The method of claim 36, wherein the energy supplying step includes shrinking of the collagen tissue of the tympanic membrane sufficiently to improve the frequency response of the tympanic membrane over at least part of a frequency range from 1 kHz to 4 kHz.

38. The method of claim 29, wherein the energy supplying step includes generating energy in the wavelength range of 1.8 to 2.55 microns.

39. The method of claim 38, wherein the energy supplying step includes generating energy in the wavelength range of 2.0 to 2.2 microns.

40. The method of claim 39, wherein the energy supplying step includes providing energy with a holmium-doped laser.

41. The method of claim 38, wherein the energy supplying step includes generating energy in the wavelength range of 1.9 to 2.1 microns.

42. The method of claim 7, wherein the energy supplying step includes providing energy with a laser diode.

* * * * *

UNITED STATES PATENT AND TRADEMARK OFFICE
CERTIFICATE OF CORRECTION

PATENT NO. : 5,591,157
DATED : January 7, 1997
INVENTOR(S) : David R. Hennings et al.

Page 1 of 2

It is certified that error appears in the above-indentified patent and that said Letters Patent is hereby corrected as shown below:

The Title Page, Section [76], Line 7 replace:
    "Calif. 91302; Stuart Harmon, 4321" with --Calif. 91302; Stuart Harman, 4321--

Column 10, Line 32, Claim 1 replace:
    "lagen absorption coefficient in a range of 10 to 1 50 $cm^{-1}$,"

with
    --lagen absorption coefficient in a range of 10 to 150 $cm^{-1}$,-

Column 11, Line 18, Claim 8 and Column 12, Line 6, Claim 21 replace:
    "5 to 10 kHz" with --5 to 10 Hz--

UNITED STATES PATENT AND TRADEMARK OFFICE
CERTIFICATE OF CORRECTION

PATENT NO. : 5,591,157
DATED : January 7, 1997
INVENTOR(S) : David R. Hennings et al.

It is certified that error appears in the above-indentified patent and that said Letters Patent is hereby corrected as shown below:

Column 11, Line 37, Claim 14 replace:
 "14. The method of claim 13, wherein the irradiating Step"
with
 --14. The method of claim 13, wherein the irradiating step--

Column 14, Line 14, Claim 42 replace:
 "42. The method of claim 7, wherein the energy supplying"
with
 --42. The method of claim 41, wherein the energy supplying--

Signed and Sealed this

Twelfth Day of September, 2000

Attest:

Q. TODD DICKINSON

*Attesting Officer*   *Director of Patents and Trademarks*